(12) United States Patent
Takehara (10) Patent No.: US 10,449,114 B2
(45) Date of Patent: Oct. 22, 2019

(54) EYE MASK-TYPE HYDROGEN SUPPLY DEVICE

(71) Applicant: Takashi Takehara, Osaka (JP)

(72) Inventor: Takashi Takehara, Osaka (JP)

( * ) Notice: Subject to any disclaimer, the term of this patent is extended or adjusted under 35 U.S.C. 154(b) by 0 days.

(21) Appl. No.: 16/068,610

(22) PCT Filed: Dec. 9, 2016

(86) PCT No.: PCT/JP2016/086768
§ 371 (c)(1),
(2) Date: Jul. 6, 2018

(87) PCT Pub. No.: WO2017/122476
PCT Pub. Date: Jul. 20, 2017

(65) Prior Publication Data
US 2019/0015296 A1    Jan. 17, 2019

(30) Foreign Application Priority Data
Jan. 12, 2016  (JP) ................. 2016-003477

(51) Int. Cl.
*A61F 7/08*    (2006.01)
*A61F 9/04*    (2006.01)
(Continued)

(52) U.S. Cl.
CPC ............... *A61H 33/14* (2013.01); *A61F 7/03* (2013.01); *A61F 7/034* (2013.01); *A61F 7/08* (2013.01); *A61F 9/04* (2013.01); *A61H 35/02* (2013.01); *A61K 8/19* (2013.01); *A61K 33/00* (2013.01); *A61Q 19/08* (2013.01); *C01B 3/08* (2013.01); *A61F 2007/0004* (2013.01);
(Continued)

(58) Field of Classification Search
CPC .............. A61H 35/02; A61H 2033/148; A61H 2201/0157; A61H 2201/0207; A61H 2201/0278; A61H 2201/10; A61H 2201/1604; A61H 2201/165; A61H 2205/022; A61H 2205/024; A61H 33/14; A61K 8/19; A61K 33/00; A61F 9/04; A61F 2007/0004; A61F 2007/0204; A61F 2007/022; A61F 2007/0228; A61F 2007/0276; A61F 7/03; A61F 7/08; A61Q 19/08; C01B 3/08; Y02E 60/36
See application file for complete search history.

(56) References Cited

U.S. PATENT DOCUMENTS

| 2003/0000517 | A1* | 1/2003 | Joseph | ............... B65D 81/3484 |
|---|---|---|---|---|
| | | | | 126/263.06 |
| 2003/0014096 | A1* | 1/2003 | Burkhart | ................... A61F 7/02 |
| | | | | 607/109 |
| 2014/0154171 | A1* | 6/2014 | Zheng | ..................... C01B 3/065 |
| | | | | 423/657 |

FOREIGN PATENT DOCUMENTS

| DE | 19730735 A1 | 2/1999 |
|---|---|---|
| JP | 2002-065714 A | 3/2002 |

(Continued)

*Primary Examiner* — Tatyana Zalukaeva
*Assistant Examiner* — Gabriella E Burnette
(74) *Attorney, Agent, or Firm* — Novick, Kim & Lee, PLLC; Jae Youn Kim (57) ABSTRACT

An eye mask-type hydrogen supply device that is freely portable when carried by a user and with which it is possible to supply hydrogen to the areas around both eyes and the eyeballs while warming the eyelids, wherein the eye mask-type hydrogen supply device can be used continuously by replacing a hydrogen gas supply pack.

10 Claims, 9 Drawing Sheets

(51) Int. Cl.
*A61F 7/03* (2006.01)
*A61H 35/02* (2006.01)
*A61K 8/19* (2006.01)
*A61K 33/00* (2006.01)
*A61F 7/00* (2006.01)
*A61F 7/02* (2006.01)
*A61H 33/14* (2006.01)
*C01B 3/08* (2006.01)
*A61Q 19/08* (2006.01)

(52) U.S. Cl.
CPC . *A61F 2007/022* (2013.01); *A61F 2007/0204* (2013.01); *A61F 2007/0228* (2013.01); *A61F 2007/0276* (2013.01); *A61H 2033/148* (2013.01); *A61H 2201/0157* (2013.01); *A61H 2201/0207* (2013.01); *A61H 2201/0278* (2013.01); *A61H 2201/10* (2013.01); *A61H 2201/1604* (2013.01); *A61H 2201/165* (2013.01); *A61H 2205/022* (2013.01); *A61H 2205/024* (2013.01); *Y02E 60/36* (2013.01)

(56) References Cited

FOREIGN PATENT DOCUMENTS

| | | |
|---|---|---|
| JP | 2014-019635 A | 2/2014 |
| WO | 2015156415 A1 | 10/2015 |

\* cited by examiner

EYE MASK-TYPE HYDROGEN SUPPLY DEVICE

TECHNICAL FIELD

The present invention relates to an eye mask-type hydrogen supply device that is capable of supplying hydrogen to the area surrounding both eyes of a user while warming the eyelids of the user.

BACKGROUND ART

In recent years, malignant active oxygen (i.e. hydroxyl radicals), which accelerates aging or causes various kinds of diseases, such as hardening of the arteries and cancer, has become an issue. The malignant active oxygen, which has very strong oxidizing power, damages cells and oxidizes (i.e. ages) the body to cause various kinds of diseases and to accelerate aging.

Hydrogen has attracted considerable attention as a means for removing malignant active oxygen from the body. The effectiveness of hydrogen has been demonstrated in various animal disease tests and in human clinical tests, and research has been actively conducted into the application of hydrogen to medical treatment. Hydrogen removes only malignant active oxygen (i.e. hydroxyl radicals), which accelerates aging or causes various kinds of diseases, such as hardening of the arteries and cancer, without producing an adverse effect on the tissues or cells of the body. Consequently, attempts to supply hydrogen into the body using a variety of methods have been made, and various clinical tests have been published. Among them, it has been found that, in the case in which a physiological salt solution saturated with hydrogen molecules is used for the administration of eye drops, the retinas are protected from retinal ischemia-reperfusion injury.

Meanwhile, the ingestion of hydrogen water, partial injection of hydrogen gas, etc. have been used as general methods of supplying hydrogen gas into the body. However, a method of directly supplying hydrogen to the eye rims of a user through simple ingestion of hydrogen has not yet been proposed, and the need therefor is expected to increase in the future.

RELATED ART DOCUMENT

Patent Document

Patent Document 1: Publication of Japanese Patent Application No. 2012-289290

Non-Patent Document

Non-Patent Document 1: Invest Ophthalmol Vis Sci 51:487-492, 2010 (Protection of the retina by rapid diffusion of hydrogen: administration of hydrogen-loaded eye drops in retinal ischemia-reperfusion injury) Oharazawa Hideaki et al.

DISCLOSURE OF THE INVENTION

Problem to be Solved by the Invention

The present invention has been made in view of the above problem, and it is an object of the present invention to provide an eye mask-type hydrogen supply device that is freely portable when carried by a user and that is capable of supplying hydrogen to the area surrounding both eyes and the eyeballs of the user while warming the eyelids of the user.

Means for Solving the Problem

In order to solve the above problem, there is provided an eye mask-type hydrogen supply device for supplying hydrogen gas and heat of reaction, which is generated at the time of generating the hydrogen gas, to the area surrounding both eyes of a user, the eye mask-type hydrogen supply device including an eye mask main body configured to be brought into contact with the region between the eyebrows of the user and with the area surrounding both eyes of the user as an eye mask, a mounting belt for connecting the eye mask main body to the face of the user, a hydrogen gas supply pack, in which aluminum hydride powder and reaction water are sealed, for reacting the aluminum hydride powder and the reaction water with each other to generate hydrogen gas and heat of reaction, and a storage pocket for mounting the hydrogen gas supply pack to the eye mask main body, wherein the hydrogen gas supply pack is replaceable for continuous use.

The hydrogen gas supply pack may be provided therein with two aluminum powder bags, in which the aluminum hydride powder is sealed and which are disposed at positions corresponding to both eyes of the user, and a reaction water bag, in which the reaction water is sealed, the aluminum powder bags and the reaction water bag being wrapped in an outer bag, and the interior of the hydrogen gas supply pack may be configured such that the reaction water bag is interposed between the two aluminum powder bags in the thickness direction thereof.

In the case in which the eye mask-type hydrogen supply device according to the present invention having the above-described construction is used, the aluminum hydride powder and the reaction water contained in the hydrogen gas supply pack, which is provided in the eye mask-type hydrogen supply device, come into contact with each other in order to induce a hydrogen gas generation reaction, whereby it is possible to generate hydrogen gas and heat of reaction. In addition, the eye mask-type hydrogen supply device according to the present invention is brought into direct contact with the region between the eyebrows of the user and the area surrounding both eyes of the user, whereby it is possible to directly supply the hydrogen gas and the heat of reaction, which are generated in the hydrogen gas supply pack, to the area surrounding both eyes of the user and to the eyeballs of the user. The hydrogen gas reaches tears covering the surfaces of the eyeballs of both eyes of the user, and slowly penetrates into the tears, whereby the tears are saturated with the hydrogen gas. The tears are changed into a fluid approximating hydrogen water and having high hydrogen density, which is considered to be identical to the case in which a physiological salt solution saturated with hydrogen molecules is used for the administration of eye drops. As a result, the density of hydrogen molecules of the vitreous bodies of the eyeballs is increased, whereby the hydrogen molecules catch malignant active oxygen present in the area surrounding the retinas and discharge the active oxygen from the body of the user. Consequently, the eye mask-type hydrogen supply device according to the present invention has the effect of protecting the retinas.

Furthermore, the heat of reaction, which is generated as the result of the generation of the hydrogen gas, is slowly transferred from the eye mask-type hydrogen supply device according to the present invention to the eyelids of the user in order to warm the area surrounding the eyes and the eyeballs of the user. As a result, the circulation of the blood in the area surrounding both eyes and the eyeballs of the user is accelerated, and it is possible to obtain an effect of very sufficiently relaxing the user through good circulation of the blood and appropriate warming. Consequently, it is not necessary for the eye mask-type hydrogen supply device according to the present invention to achieve antinomic objects, such as restraining the generation of heat at the time of generating hydrogen and securing the amount of hydrogen that is generated. On the contrary, both an increase in the amount of hydrogen that is generated and the generation of heat are utilized.

Furthermore, in the eye mask-type hydrogen supply device according to the present invention having the above-described construction, each of the aluminum powder bags and the reaction water bag may be made of an aluminum laminate material. In addition, the outer bag may be made of a waterproof moisture-permeable material, such as GORE-TEX (Registered Trademark).

Since the hydrogen gas suction tool according to the present invention having the above-described construction is used, the aluminum powder bags and the reaction water bag exhibit the properties of a strong barrier to liquid, gas, and vapor. For this reason, it is possible to prevent the contents of the reaction water bag and the aluminum powder bags from leaking to the outside, and it is also possible to prevent external liquid, gas, and vapor from penetrating into the respective bags. In particular, the aluminum hydride powder received in the aluminum powder bags contact water and vapor to generate hydrogen gas. In order to prevent the generation of undesired hydrogen gas, therefore, each bag may be made of an aluminum laminate material. Furthermore, in the case in which the outer bag is made of a waterproof moisture-permeable material, aluminum or water is prevented from leaking to the outside, and only hydrogen and vapor can be discharged to the outside at the time of reaction.

Furthermore, in the eye mask-type hydrogen supply device according to the present invention having the above-described construction, non-woven fabric may be inserted into each of the aluminum powder bags.

Since the hydrogen gas suction tool according to the present invention having the above-described construction is used, the reaction water that has penetrated into the aluminum powder bags is absorbed into the entirety of the non-woven fabric. Consequently, it is possible to effectively accelerate the generation of hydrogen gas without placing the aluminum hydride powder and the reaction water in the aluminum powder bags in a biased state.

Furthermore, in the eye mask-type hydrogen supply device according to the present invention having the above-described construction, the mounting belt may be provided with a belt adjustment portion, and the user may manipulate the belt adjustment portion in order to adjust the length of the mounting belt in consideration of the circumference of the head of the user.

Since the hydrogen gas suction tool according to the present invention having the above-described construction is used, the eye mask-type hydrogen supply device according to the present invention may be fixed with appropriate tension without the risk of the eye mask-type hydrogen supply device according to the present invention becoming separated from the face of the user or without the user experiencing discomfort due to the mounting of the eye mask-type hydrogen supply device according to the present invention on the head of the user.

Furthermore, the interior of the outer bag may be filled with nitrogen gas. In the case in which the interior of the outer bag is filled with nitrogen gas, it is possible to prevent atmospheric moisture in the environment from penetrating into the outer bag during the storage of the eye mask-type hydrogen supply device according to the present invention in a storehouse, etc., whereby it is possible to preserve the eye mask-type hydrogen supply device according to the present invention for a long time.

In addition, the gap between the outer bag and each of the aluminum powder bags may be filled with a polymer absorbent. For example, the gap between the outer bag and each of the aluminum powder bags may be filled with a polymer absorbent made of an absorptive polymer, such as silica gel. Since the surface of the polymer absorbent is porous, the polymer absorbent absorbs water through the pores at room temperature, but the polymer absorbent discharges moisture (vapor) through the pores when the temperature of each of the aluminum powder bags is increased as the result of hydrogen generation reaction. At room temperature, therefore, the polymer absorbent absorbs the reaction water, whereby it is possible to prevent the reaction water from leaking to the outside. At the time of reaction, on the other hand, the polymer absorbent discharges vapor, whereby it is possible to discharge the vapor and hydrogen through the outer bag. The vapor becomes hydrogen water, which reaches the eyeballs of the user, whereby it is possible to rapidly achieve the same effect as the administration of hydrogen water-loaded eye drops.

In addition, the hydrogen gas supply pack of the eye mask-type hydrogen supply device according to the present invention may be provided therein with an aluminum powder bag, in which the aluminum hydride powder is sealed and which is disposed at positions corresponding to both eyes of the user, and a reaction water bag, in which the reaction water is sealed and which is disposed so as to overlap the aluminum powder bag in the thickness direction thereof, and each of the gap between the outer bag and the aluminum powder bag and the gap between the outer bag and the reaction water bag may be filled with a polymer absorbent.

In the eye mask-type hydrogen supply device according to the present invention, it is sufficient to dispose the aluminum powder bag and the reaction water bag so as to overlap each other. The reason for this is that it is sufficient to dispose the aluminum powder bag on the eye side, since the leakage of moisture is prevented by the polymer absorbent, as described above.

Furthermore, the polymer absorbent may be formed in a sheet shape, and may be interposed in the gap between the outer bag and the aluminum powder bag.

BRIEF DESCRIPTION OF THE DRAWINGS

FIGS. 2A and 2B are views illustrating the construction of an eye mask main body shown in FIG. 1, wherein

FIGS. 3A and 3B are views illustrating the construction of a hydrogen gas supply pack 11 shown in FIG. 1, wherein

FIGS. 4A, 4B and 4C are views illustrating a method of using the eye mask-type hydrogen supply device according to the present invention, wherein FIGS. 5A and 5B are sectional views showing an example in which a polymer absorbent is interposed as a modification of the hydrogen gas supply pack shown in FIGS. 3A, 3B, 4A, 4B and 4C, wherein

BEST MODE FOR CARRYING OUT THE INVENTION

Hereinafter, exemplary embodiments of an eye mask-type hydrogen supply device according to the present invention will be described in detail with reference to FIGS. 1 to 4. However, the present invention is not limited to the illustrated embodiments. In addition, the drawings are provided to conceptually describe the present invention. For easy comprehension, therefore, dimensions, ratios, or numbers may be exaggerated or simplified as needed. Furthermore, in the following description, the same reference numbers will be used to refer to the same or like parts, a duplicate description of which will be omitted.

Figure 1:
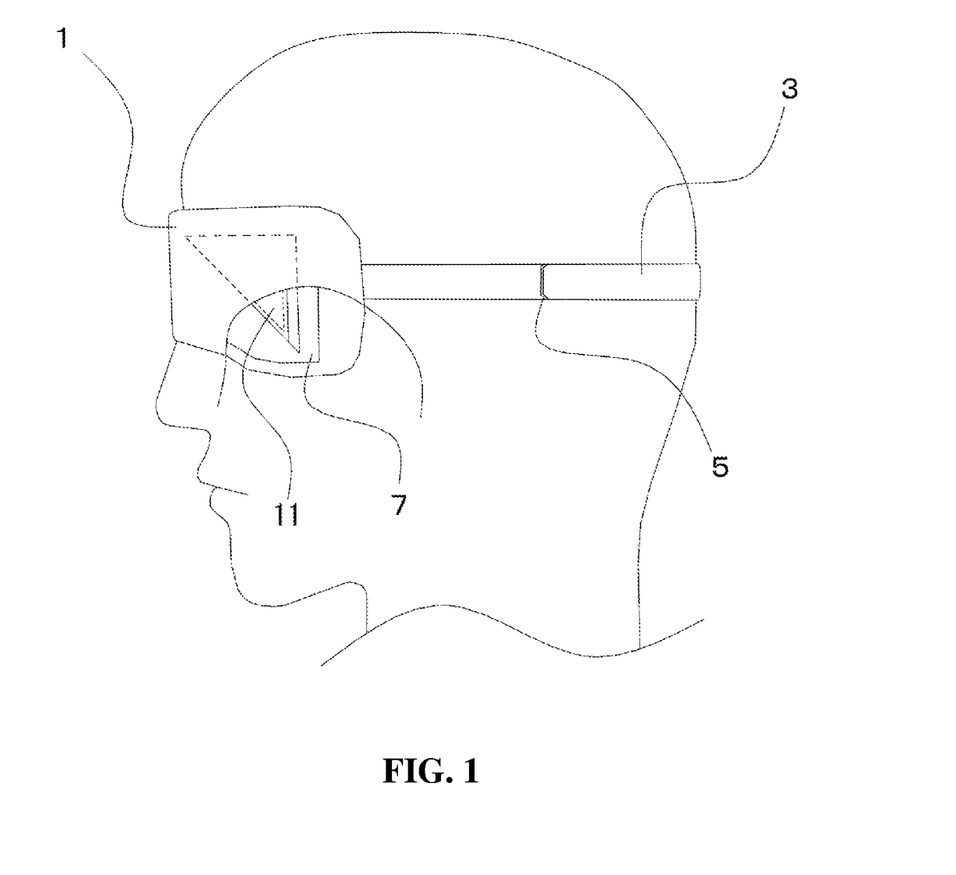
FIG. 1 is a schematic view showing the outline of an eye mask-type hydrogen supply device according to the present invention.

First, the outline of an eye mask-type hydrogen supply device according to the present invention will be described with reference to FIG. 1. FIG. 1 is a schematic view showing the outline of the eye mask-type hydrogen supply device according to the present invention. As shown in FIG. 1, the eye mask-type hydrogen supply device according to the present invention is used in the state of being mounted on the face of a user. Hydrogen gas is generated from a hydrogen gas supply pack 11 provided in the eye mask-type hydrogen supply device according to the present invention.

In addition, the hydrogen gas supply pack 11, from which hydrogen gas has been generated, may be removed from the eye mask-type hydrogen supply device according to the present invention, and may be replaced with a new hydrogen gas supply pack 11. Consequently, it is possible for the user to continuously use the eye mask-type hydrogen supply device according to the present invention.

The eye mask-type hydrogen supply device according to the present invention mainly includes an eye mask main body 1, a mounting belt 3 for connecting the eye mask main body 1 to the face of the user, a belt adjustment unit 5 for adjusting the length of the mounting belt 3, a storage pocket 7 for storing a hydrogen gas supply pack 11 in the eye mask main body 1, and a hydrogen gas supply pack 11 for generating hydrogen gas.

Figure 2A:
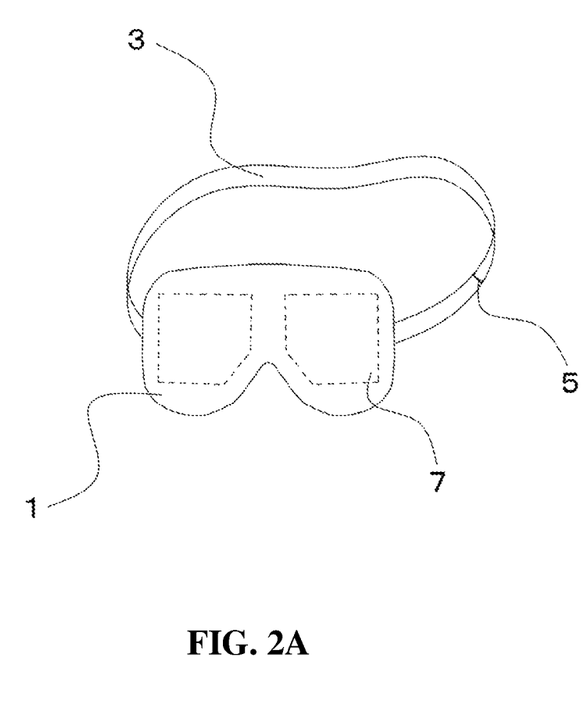
FIG. 2A is a schematic view showing the entirety of the eye mask main body and FIG. 2B is a partial sectional view showing the interior of the eye mask main body.
Figure 2B:
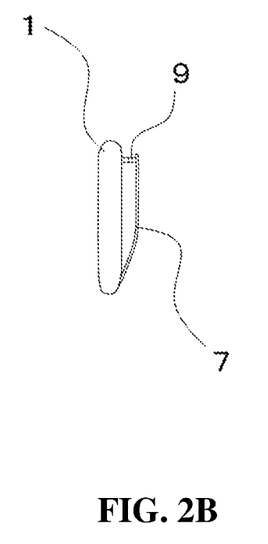

Next, the eye mask main body will be described in detail with reference to FIGS. 2A and 2B. FIGS. 2A and 2B are views illustrating the construction of the eye mask main body 1 shown in FIG. 1, wherein FIG. 2A is a schematic view showing the entirety of the eye mask main body 1 and FIG. 2B is a partial sectional view showing the interior of the eye mask main body 1.

As shown in FIGS. 2A and 2B, the eye mask main body 1 is an eye mask that contacts the portion between the eyebrows and the area surrounding both eyes (the portion between the upper part of each cheekbone and a supraorbital ridge corresponding thereto) on the face of the user. The eye mask main body 1 is made of cloth fiber that does not stimulate the skin of the user (for example, cotton or TEMPUR®). In addition, a cushion (not shown), made of urethane foam, for improving the user's wearing sensation and preventing direct contact between the eye mask main body 1 and the eyelids of the user, may be provided at the edge of the eye mask main body 1 that contacts the face of the user.

The mounting belt 3, which connects the eye mask-type hydrogen supply device according to the present invention to the face of the user, is provided at the eye mask main body 1, and the two ends of the mounting belt 3 are connected respectively to the left and right ends of the eye mask main body 1. The mounting belt 3 is made of a stretchable material, such as a power net or a satin net, including polyurethane elastic fiber, or is made of natural rubber that is used for clothes.

In addition, the belt adjustment unit 5, such as a hook-and-loop fastener or a buckle, is provided at the mounting belt 3 such that the user can adjust the entire length of the mounting belt 3 in consideration of the circumference of the head of the user.

As shown in FIG. 2B, the storage pocket 7, which serves to store the hydrogen gas supply pack 11, is provided at the side of the eye mask main body 1 that contacts the face of the user. The storage pocket 7 is configured such that two hydrogen gas supply packs 11 are disposed right above the left and right eyelids of the user, respectively. In the area right above the region between the eyebrows, a single storage pocket 7 may be partitioned into two storage units. Alternatively, two storage pockets 7 may be provided right above the left and right eyelids of the user, respectively.

An opening defined by the eye mask main body 1 and the storage pocket 7 is provided with a sealing portion 9, which seals (encapsulates) the hydrogen gas supply pack 11, which is stored in the storage pocket 7, in order to prevent the hydrogen gas supply pack 11 from being separated and discharged to the outside. The sealing portion 9 is made of a hook-and-loop fastener or a zipper of the type used for clothes. Consequently, it is possible for the user to easily open and close the opening defined by the eye mask main body 1 and the storage pocket 7.

Figure 3A:
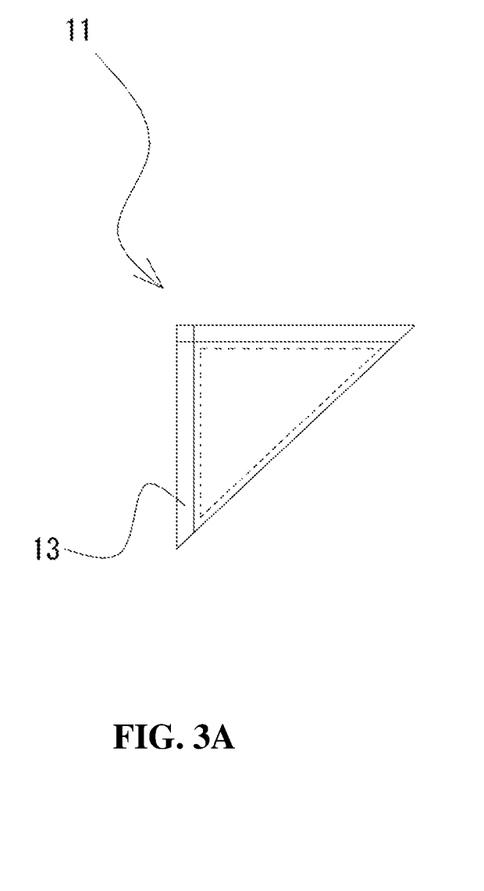
FIG. 3A is a front view showing the entirety of the hydrogen gas supply pack 11 and FIG. 3B is a sectional view showing the interior of the hydrogen gas supply pack 11.
Figure 3B:
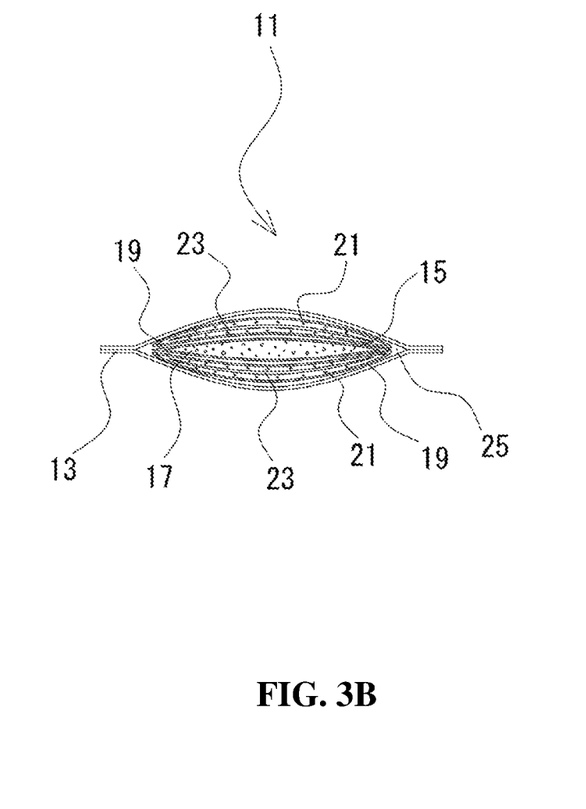

Next, the hydrogen gas supply pack 11 will be described in detail with reference to FIGS. 3A and 3B. FIGS. 3A and 3B are views illustrating the construction of the hydrogen gas supply pack 11 shown in FIG. 1, wherein FIG. 3A is a front view showing the entirety of the hydrogen gas supply pack 11 and FIG. 3B is a sectional view showing the interior of the hydrogen gas supply pack 11.

As shown in FIG. 3A, the hydrogen gas supply pack 11 is a pack covered by an outer bag 13. The hydrogen gas supply pack 11 is shown as being formed in an approximately triangular shape in FIG. 3A. Alternatively, the hydrogen gas supply pack 11 may be formed in a polygonal shape or an approximately circular shape. In the hydrogen gas supply pack 11 are inserted aluminum hydride powder 21 ($AlH_3$) and reaction water 17, which will be described later, in the state of being isolated from each other. The aluminum hydride powder 21 ($AlH_3$) and the reaction water 17 may react with each other to generate hydrogen gas and heat of reaction ($2AlH_3 + 3H_2O \rightarrow Al_2O_3 + 6H_2$).

Next, as shown in FIG. 3B, a reaction water bag 15 filled with the reaction water 17, two aluminum powder bags 19, in which the aluminum hydride powder 21 and non-woven fabric 23 are received, respectively, and nitrogen gas 25 for preventing the penetration of moisture in the air are inserted (encapsulated) in the hydrogen gas supply pack 11. In addition, the reaction water bag 15 is disposed in the state of being interposed between the two aluminum powder bags 19.

The outer bag 13, the reaction water bag 15, and the aluminum powder bags 19, which are high-barrier laminate bags that are manufactured by laminating aluminum, exhibit the properties of a strong barrier to liquid, gas, and vapor. For this reason, it is possible to prevent the contents of the reaction water bag 15 and the aluminum powder bags 19 from leaking to the outside, and it is also possible to prevent liquid, gas, and vapor from penetrating into the reaction water bag 15 and the aluminum powder bags 19.

The aluminum hydride powder 21 received in the aluminum powder bags 19 contact water and vapor to generate hydrogen gas. In order to prevent the generation of undesired hydrogen gas, therefore, it is very effective to use high-barrier laminate bags that exhibit strong barrier properties.

When in use, the user punches holes in the outer bag 13 of the hydrogen gas supply pack 11, the reaction water bag 15 and the aluminum powder bags 19 in the hydrogen gas supply pack 11 using a needle 31 such that the aluminum hydride powder 21 and the reaction water 17 can contact each other.

The reaction water 17 in the reaction water bag 15 reaches the interior of the aluminum powder bags 19 through the holes formed by the needle 31, and comes into contact with the aluminum hydride powder 21 in the aluminum powder bags 19. Hydrogen gas generated in the aluminum powder bags 19 is discharged out of the outer bag 13 through the holes formed in the aluminum powder bags 19 and the outer bag 13. In addition, heat of reaction generated as the result of the generation of the hydrogen gas is transferred from the aluminum powder bags 19 to the outer bag 13, and is then dissipated to the outside.

The aluminum hydride powder 21 received in the aluminum powder bags 19 is uniformly distributed in the non-woven fabric 23, which is also received in the aluminum powder bags 19. For this reason, the reaction water 17 that has penetrated into the aluminum powder bags 19 is absorbed into the entirety of the non-woven fabric 23. Consequently, it is possible to effectively accelerate the generation of hydrogen gas without placing the aluminum hydride powder 21 and the reaction water 17 in the aluminum powder bags 19 in a biased state.

Figure 4A:
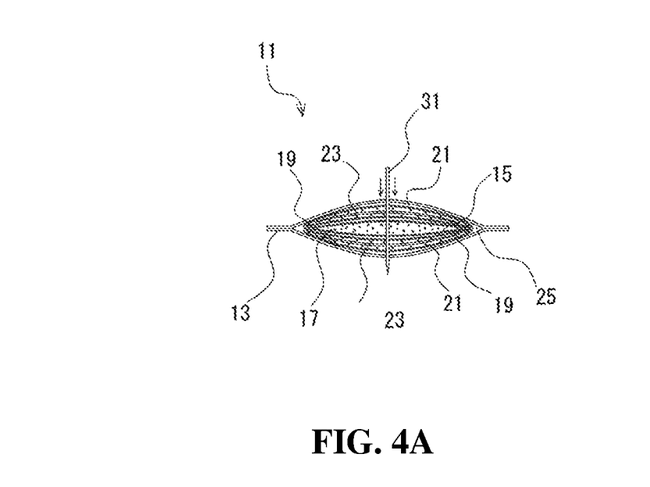
FIG. 4A is a sectional view showing a method of preparing to use the hydrogen gas supply pack 11.
Figure 4B:
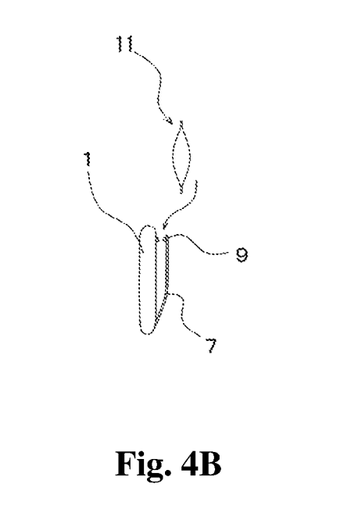
FIG. 4B is a sectional view showing a method of storing the hydrogen gas supply pack 11 in a storage pocket 7 provided in the eye mask main body 1.
Figure 4C:
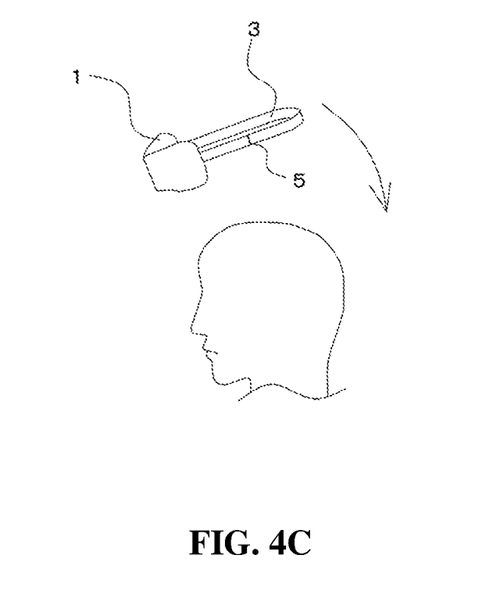
FIG. 4C is a schematic view showing a method of mounting the eye mask-type hydrogen supply device according to the present invention, which is performed by a user.

Next, a method of using the eye mask-type hydrogen supply device according to the present invention will be described in detail with reference to FIGS. 4A, 4B and 4C. FIGS. 4A, 4B and 4C are views illustrating a method of using the eye mask-type hydrogen supply device according to the present invention, wherein FIG. 4A is a sectional view showing a method of preparing to use the hydrogen gas supply pack 11, FIG. 4B is a sectional view showing a method of storing the hydrogen gas supply pack 11 in the storage pocket 7 provided in the eye mask main body 1, and FIG. 4C is a schematic view showing a method of mounting the eye mask-type hydrogen supply device according to the present invention, which is performed by the user.

As shown in FIG. 4A, first, the user punches a plurality of holes in the outer bag 13, the aluminum powder bags 19, and the reaction water bag 15 of the hydrogen gas supply pack 11 using the needle 31. The needle 31 is shown as being a general needle in FIG. 4A. Alternatively, dedicated parts (not shown) for forming holes may be provided in the respective bags such that the user simply folds or pushes the hydrogen gas supply pack 11 to punch holes in the respective bags.

Subsequently, as shown in FIG. 4B, the hydrogen gas supply pack 11 is stored in the storage pocket 7, which is provided in the eye mask main body 1. The user opens the sealing portion 9, which is provided between the eye mask main body 1 and the storage pocket 7, in order to store the hydrogen gas supply pack 11 in the storage pocket 7. After the hydrogen gas supply pack 11 is stored in the storage pocket 7, the user closes the sealing portion 9 and mounts the hydrogen gas supply pack 11 to the storage pocket 7.

Subsequently, as shown in FIG. 4C, the eye mask-type hydrogen supply device according to the present invention is mounted on the face of the user. First, the user checks the orientation of the eye mask main body 1 and brings the eye mask main body 1 into contact with the region between the eyebrows and the area surrounding both eyes. Subsequently, the user passes the mounting belt 3 through the top of the head of the user and manipulates the belt adjustment unit 5 in order to adjust the length of the mounting belt 3 in consideration of the circumference of the head of the user. As a result, the eye mask-type hydrogen supply device according to the present invention is fixed with appropriate tension without the risk of the eye mask-type hydrogen supply device according to the present invention becoming separated from the face of the user or without the user experiencing discomfort due to the mounting of the eye mask-type hydrogen supply device according to the present invention, whereby normal mounting of the eye mask-type hydrogen supply device according to the present invention is completed.

Hydrogen gas generated in the eye mask-type hydrogen supply device according to the present invention is supplied to the area surrounding both eyes of the user, and reaches tears covering the surfaces of the eyeballs of both eyes of the user. As the hydrogen gas slowly penetrates into the tears and thus the tears are saturated with the hydrogen gas, the tears are changed into a fluid approximating hydrogen water and having high hydrogen density. As a result, the eyeballs are covered with the fluid approximating hydrogen water. The fluid approximating hydrogen water increases the density of hydrogen molecules of the vitreous bodies of the eyeballs, whereby the hydrogen molecules catch active oxygen present in the area surrounding the retinas and discharge the active oxygen from the body of the user.

In addition, the tears that have become the fluid approximating hydrogen water have very excellent effects of restraining oxidative stress or apoptosis of retinal neurons, reducing the thickness of the retinas, and effectively restraining the activation of glial cells.

Furthermore, heat of reaction generated as the result of the generation of the hydrogen gas is slowly transferred from the eye mask-type hydrogen supply device according to the present invention to the eyelids of the user in order to warm the area surrounding both eyes and the eyeballs of the user. As a result, the circulation of the blood in the area surrounding both eyes and the eyeballs of the user is accelerated. Consequently, it is possible to obtain an effect of very sufficiently relaxing the user through good circulation of the blood and appropriate warming.

Although the embodiment of the eye mask-type hydrogen supply device according to the present invention has been described by way of example, the present invention is not limited to the described embodiment, and those skilled in the art will appreciate that other improvements and modifications are possible, without departing from the scope and spirit of the invention as disclosed in the accompanying claims.

Figure 5A:
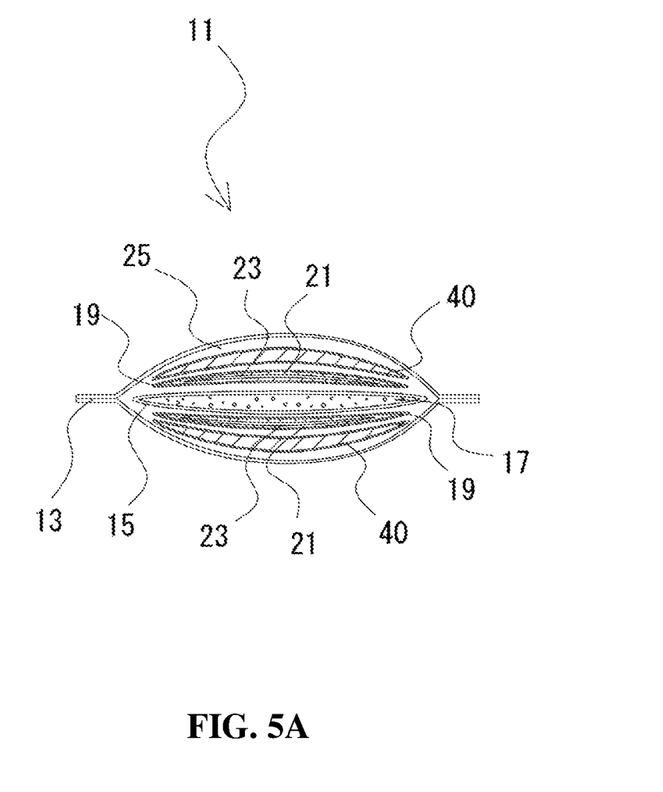
FIG. 5A is a view showing an example in which a polymer absorption sheet is interposed between an outer bag and each aluminum powder bag both on the eye side (the upper side of the figure) and on the rear thereof and FIG. 5B is a view showing an example in which a polymer absorption sheet is interposed between the outer bag and each aluminum powder bag only on the eye side.
Figure 5B:
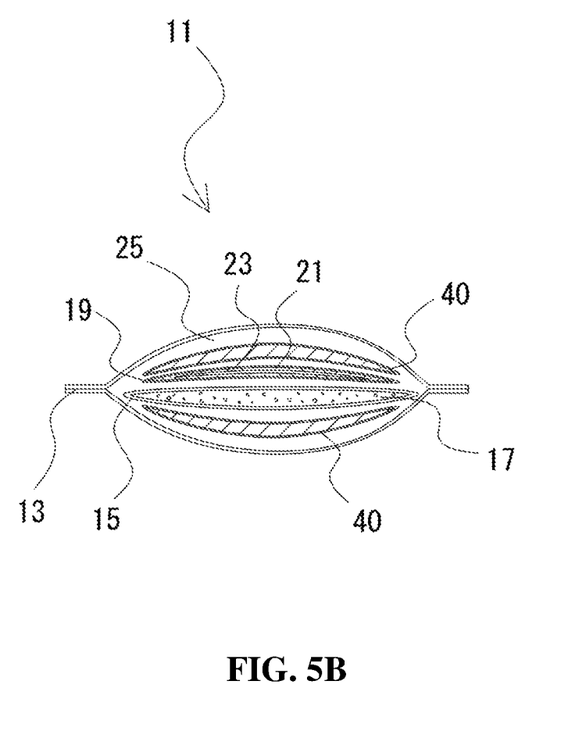

For example, in the eye mask-type hydrogen supply device described above, the interior of the outer bag 13 is filled with the nitrogen gas 25. In addition, the gap between the outer bag 13 and each of the aluminum powder bags 19 may be filled with a polymer absorbent. FIGS. 5A and 5B are sectional views showing an example in which a polymer absorbent is interposed as a modification of the hydrogen gas supply pack 11 shown in FIGS. 3A, 3B, 4A, 4B and 4C, wherein FIG. 5A is a view showing an example in which a polymer absorption sheet 40 is interposed between the outer bag 13 and each of the aluminum powder bags 19 both on the eye side (the upper side in the figure) and on the rear thereof, and FIG. 5B is a view showing an example in which a polymer absorption sheet 40 is interposed between the outer bag 13 and each of the aluminum powder bags 19 only on the eye side.

The polymer absorption sheet 40 is a bag member having an absorptive polymer, such as silica gel, contained therein. The outer bag of the bag member is made of a waterproof moisture-permeable material, such as GORE-TEX (Registered Trademark). The waterproof moisture-permeable material may be used to form the outer bag 13, the aluminum powder bags 19, and the reaction water bag 15. In addition, the interior of the outer bag 13 may be directly filled with an absorptive polymer, although the polymer absorption sheet 40 is interposed between the outer bag 13 and each of the aluminum powder bags 19 in the example of FIGS. 5A and 5B.

INDUSTRIAL APPLICABILITY

The eye mask-type hydrogen supply device according to the present invention is configured to be brought into direct contact with the region between the eyebrows of the user and the area surrounding both eyes of the user. Consequently, the aluminum hydride powder and the reaction water contained in the hydrogen gas supply pack, which is provided in the eye mask-type hydrogen supply device, come into direct contact with each other in order to generate hydrogen gas. The hydrogen gas and heat of reaction, which is generated as the result of the generation of the hydrogen gas, can be directly supplied to the area surrounding both eyes of the user and to the eyeballs of the user. The hydrogen gas catches malignant active oxygen present in the area surrounding the eyes of the user and around the eyeballs of the user and discharges the caught active oxygen from the body of the user. Furthermore, the heat of reaction, which is generated as the result of the generation of the hydrogen gas, is transferred to the eyelids of the user in order to warm the area surrounding the eyes and the eyeballs of the user. As a result, the circulation of the blood in the area surrounding both eyes and the eyeballs of the user is accelerated. Consequently, it is possible to obtain an effect of very sufficiently relaxing the user through good circulation of the blood and appropriate warming.

DESCRIPTION OF REFERENCE NUMERALS

1 Eye mask main body
3 Mounting belt
5 Belt adjustment unit
7 Storage pocket
9 Sealing portion
11 Hydrogen gas supply pack
13 Outer bag
15 Reaction water bag
17 Reaction water
19 Aluminum powder bags
21 Aluminum hydride powder
23 Non-woven fabric
25 Nitrogen gas
31 Needle

The invention claimed is:

1. An eye mask-type hydrogen supply device for supplying hydrogen gas and heat of reaction, which is generated at a time of generating the hydrogen gas, to an area surrounding both eyes of a user, the eye mask-type hydrogen supply device comprising:
   an eye mask main body configured to be brought into contact with a portion between eyebrows of the user and with the area surrounding the both eyes of the user as an eye mask;
   a mounting belt for connecting the eye mask main body to a face of the user;
   a hydrogen gas supply pack, in which aluminum hydride powder and reaction water are sealed, for reacting the aluminum hydride powder and the reaction water with each other to generate the hydrogen gas and the heat of reaction; and
   a storage pocket for mounting the hydrogen gas supply pack to the eye mask main body, wherein the hydrogen gas supply pack is replaceable for continuous use.

2. The eye mask-type hydrogen supply device according to claim 1, wherein the hydrogen gas supply pack is provided therein with two aluminum powder bags, in which the aluminum hydride powder is sealed and which are disposed at positions corresponding to the both eyes of the user, and a reaction water bag, in which the reaction water is sealed, the aluminum powder bags and the reaction water bag being wrapped in an outer bag, and
   an interior of the hydrogen gas supply pack is configured such that the reaction water bag is interposed between the two aluminum powder bags in a thickness direction thereof.

3. The eye mask-type hydrogen supply device according to claim 2, wherein each of the aluminum powder bags and the reaction water bag is made of an aluminum laminate material.

4. The eye mask-type hydrogen supply device according to claim 2, wherein the outer bag is made of a waterproof moisture-permeable material.

5. The eye mask-type hydrogen supply device according to claim 2, wherein non-woven fabric is inserted in each of the aluminum powder bags.

6. The eye mask-type hydrogen supply device according to claim 2, wherein
   the mounting belt is provided with a belt adjustment portion, and
   the user manipulates the belt adjustment portion in order to adjust a length of the mounting belt in consideration of a circumference of a head of the user.

7. The eye mask-type hydrogen supply device according to claim 2, wherein an interior of the outer bag is filled with nitrogen gas.

8. The eye mask-type hydrogen supply device according to claim 2, wherein a gap between the outer bag and each of the aluminum powder bags is filled with a polymer absorbent.

9. The eye mask-type hydrogen supply device according to claim 1, wherein the hydrogen gas supply pack is provided therein with an aluminum powder bag, in which the aluminum hydride powder is sealed and which is disposed at positions corresponding to the both eyes of the user, and a reaction water bag, in which the reaction water is sealed and which is disposed so as to overlap the aluminum powder bag in a thickness direction thereof, the aluminum powder bag and the reaction water bag being wrapped in an outer bag, and each of a gap between the outer bag and the aluminum powder bag and a gap between the outer bag and the reaction water bag is filled with a polymer absorbent.

10. The eye mask-type hydrogen supply device according to claim 9, wherein the polymer absorbent is formed in a sheet shape, and is interposed in the gap between the outer bag and the aluminum powder bag.

* * * * *